United States Patent [19]

Budt et al.

[11] Patent Number: 5,198,544
[45] Date of Patent: Mar. 30, 1993

[54] PROCESS FOR THE PREPARATION OF PENEM COMPOUNDS

[75] Inventors: Karl-Heinz Budt, Kelkheim/Taunus; Walter Dürokheimer, Hattersheim am Main; Gerd Fischer, Frankfurt am Main; Rolf Hörlein; Reiner Kirrstetter, both of Kelkheim/Taunus; Rudolf Lattrell, Königstein/Taunus, all of Fed. Rep. of Germany

[73] Assignee: Hoechst Aktiengesellschaft, Frankfurt am Main, Fed. Rep. of Germany

[21] Appl. No.: 659,488

[22] Filed: Feb. 25, 1991

Related U.S. Application Data

[63] Continuation of Ser. No. 515,234, Apr. 27, 1990, abandoned.

[30] Foreign Application Priority Data

Apr. 29, 1989 [DE] Fed. Rep. of Germany ....... 3914389
May 27, 1989 [DE] Fed. Rep. of Germany ....... 3917287

[51] Int. Cl.$^5$ .............................................. C07D 499/00
[52] U.S. Cl. ................................... 540/310; 540/311; 540/312
[58] Field of Search .................. 514/210; 540/310, 350

[56] References Cited

U.S. PATENT DOCUMENTS 4,692,442 9/1987 Gostelli .............................. 540/310
4,794,109 12/1988 Lany ................................. 514/192

FOREIGN PATENT DOCUMENTS 0275002 1/1988 European Pat. Off. .
3429102A1 8/1983 Fed. Rep. of Germany .

OTHER PUBLICATIONS

"New Synthesis of Penems, the Oxalimide Cyclization Reaction," Afonso et al., J. Am. Chem. Soc. 1982, 104, pp. 6138–6139.

Primary Examiner—Nicholas S. Rizzo
Attorney, Agent, or Firm—Finnegan, Henderson, Farabow, Garrett and Dunner

[57] ABSTRACT

Compound I

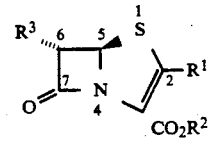

is obtained by reaction of compound II

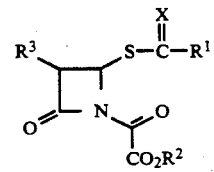

with compound III

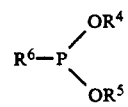

3 Claims, No Drawings

PROCESS FOR THE PREPARATION OF PENEM COMPOUNDS

This application is a continuation of application Ser. No. 07/515,234, filed Apr. 27, 1990 now abandoned.

The invention relates to a process for the preparation of penem compounds.

Penem derivatives of the formula I are valuable compounds with antibiotic properties. A synthetic process disclosed in the literature for penem derivatives I entails intramolecular cyclization of azetidinone derivatives of the formula II with trialkyl phosphites. However, this process often provides only poor yields. Moreover, the reaction is slow and requires elevated reaction temperatures, for example reflux in toluene. Under these reaction conditions there is frequently partial inversion of configuration at C-5, which results in undesired (5S,6S)-penems.

It has now been found that the described disadvantages of the known process can be avoided if dialkyl alkylphosphonites are used in place of trialkyl phosphites for the cyclization reaction. These novel reagents permit the reaction temperatures to be lower, for example room temperature, and result in shorter reaction times. Higher yields and purer products are achieved thereby. In addition, the undesired isomerization to (5S,6S)-penems is avoided. The dialkyl alkylphosphonates and dialkyl alkylthiophosphonates formed as by-products can be removed in a straightforward manner.

Hence the invention relates to a process for the preparation of penem derivatives of the formula I, in which the preferred configuration is (5R,6S)

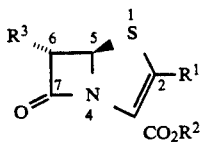

and in which
$R^1$ denotes hydrogen, $(C_1-C_4)$-alkyl, $(C_1-C_{12})$-alkoxy, $(C_1-C_{12})$-alkylthio, phenoxy, phenyl (the phenyl rings being unsubstituted or substituted once or twice by carboxyl, $(C_1-C_4)$-alkoxycarbonyl, allyloxycarbonyl, aminocarbonyl, $(C_1-C_4)$)-alkylaminocarbonyl, cyano, F, Cl or Br), $(C_3-C_6)$-cycloalkyl, $(C_3-C_6)$-cycloalkyloxy, $(C_5-C_6)$-oxacycloalkyl (saturated or singly or doubly unsaturated), $(C_3-C_6)$-oxocycloalkyl, $(C_3-C_6)$-[1,1-bis($C_1-C_3$)-alkyloxy]-cycloalkyl, $(C_3-C_6)$-[($C_1-C_3$)-alkylimino]-cycloalkyl, $(C_3-C_6)$-[arylimino]cycloalkyl, $(C_3-C_6)$-hydroxyiminocycloalkyl, $(C_3-C_6)$-($C_1-C_3$-alkyloxyimino)-cycloalkyl, in which the cycloalkyl radical is unsubstituted or substituted once or twice by $C_1-C_3$-alkyl, preferably methyl, by $(C_1-C_3)$alkoxy, preferably methoxy, by halogen, preferably chlorine, or by methylene and is saturated or can contain one or two double bonds,
$R^2$ denotes hydrogen or a customary carboxyl protective group which can be eliminated by hydrolysis, photolysis, oxidation, reduction or enzymatically,
$R^3$ denotes hydrogen, $(C_1-C_4)$-alkyl, $(C_1-C_4)$-alkenyl, $(C_1-C_4)$-alkoxy, $(C_4-C_7)$-cycloalkyl, phenyl, 2-oxo-1,3-dioxolyl, triazolyl, thiazolyl, amino, acylamino or alkoxy.

Suitable and particularly preferred substituents are the following:

$R^1$ hydrogen, $(C_1-C_4)$-alkyl (for example methyl, ethyl, hydroxymethyl and aminomethyl), $(C_1-C_4)$-alkoxy (for example methoxy and ethoxy), $(C_1-C_3)$-alkylthio (for example methylthio, ethylthio and propylthio), phenoxy (for example 4-carboxamidophenoxy or 4-cyanophenoxy), phenyl (for example 4-carboxamidophenyl or 4-cyanophenyl), saturated or unsaturated $(C_5-C_6)$-oxacycloalkyl (for example tetrahydrofuryl or furyl), $(C_5-C_6)$-oxocycloalkyl (for example 1-oxo-3-cyclobutyl), 3-hydroxyiminocyclobutyl, 3-methoxyiminocyclobutyl and 3,3-dimethoxycyclobutyl.
$R^3$ 1-hydroxyethyl (in which the OH group is free or protected by trimethylsilyl, diphenyl-tert.-butylsilyl, allyloxycarbonyl, trichloroethyloxycarbonyl or 4-nitrobenzyloxycarbonyl), $(C_1-C_3)$-alkoxy (for example methoxy or ethoxy), $(C_1-C_3)$-alkenyl, for example triazolylethylene or thiazolylethylene.

The $(C_1-C_4)$-alkyl and $(C_1-C_4)$-alkoxy groups in the substitutent $R^1$ are either unsubstituted or substituted once or twice by hydroxyl, $(C_1-C_4)$-alkoxy, $(C_1-C_4)$-acyloxy, amino, $(C_1-C_4)$-alkylamino, $(C_1-C_4)$-acylamino, mercapto, $(C_1-C_4)$-alkylthio or heterocyclylthio, for example thiazolyl-, thiadiazolyl-, pyridylthio.

Phenyl nuclei are likewise unsubstituted or substituted once or twice by carboxyl, $(C_1-C_4)$-alkoxycarbonyl, allyloxycarbonyl, aminocarbonyl, $(C_1-C_4)$-alkylaminocarbonyl, cyano or halogen, preferably F, Cl, Br.

The $(C_1-C_4)$-alkyl and $(C_1-C_4)$-alkoxy groups in $R^3$ are either unsubstituted or substituted by hydroxyl, $(C_1-C_4)$-alkoxy, $(C_1-C_4)$-acyloxy, amino, $(C_1-C_4)$-alkylamino, $(C_1-C_4)$-acylamino, mercapto, $(C_1-C_4)$-alkylthio or heterocyclylthio, it being possible for an OH group to be free or protected by trimethylsilyl, diphenyl-tert.-butylsilyl, allyloxycarbonyl, trichloroethoxycarbonyl or 4-nitrobenzyloxycarbonyl.

In the process according to the invention, the compounds of the formula I are prepared by reacting a compound of the formula II

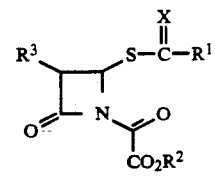

in which
X denotes oxygen or sulfur, and
$R^1$, $R^2$ and $R^3$ have the above meaning, with a trivalent organic phosphorus compound of the formula III

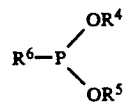

in which
$R^6$ denotes $(C_1-C_4)$-alkyl, for example methyl, ethyl or trifluoromethyl, phenyl which can be substituted by $(C_1-C_3)$-alkyl or $(C_1-C_3)$-alkoxy, and
$R^4$ and $R^5$ are identical or different and denote $(C_1-C_4)$-alkyl, allyl, benzyl, or phenyl which can be substituted by $(C_1-C_3)$-alkyl or $(C_1-C_3)$-alkoxy.

The reaction between a compound II and a compound III can be carried out in a suitable organic solvent, for example in tetrahydrofuran, ethyl acetate, an aromatic hydrocarbon such as benzene, toluene or xylene, or a halogenated hydrocarbon such as dichloromethane, trichloromethane or 1,1,2-trichloroethane.

The reaction temperature can vary between +10° C. and 160° C., preferably between +20° C. and +70° C.

The concentration of the compound II to be cyclized is between 1 mmol/l and 100 mmol/l, preferably between 2 mmol/l and 20 mmol/l.

The amount of the compound III can be between 2 and 8 mole-equivalents, preferably between 2 and 6 mole-equivalents, relative to II.

The compounds of the formulae II and III are known or can be prepared by processes disclosed in the literature.

The examples which follow serve to illustrate the invention further.

EXAMPLE 1

4-Nitrobenzyl (5R,6S)-6-[(1R)-tert.-butyldimethylsilyloxyethyl]-2-(4-aminocarbonylphenoxy)penem-3-carboxylate 130 mg (0.2 mmol) of (3S,4R)-4-[(aminocarbonyl)-phenoxythiocarbonylthio]-3-[(1R)-tert.-butyldimethyl-silyloxyethyl)]-1-(4-nitrobenzyloxycarbonyl)-azetidin-2-one were dissolved in 90 ml of $CHCl_3$ under an argon atmosphere at 55° C. To this was added within 30 minutes a solution of 90 mg (0.8 mmol) of dimethyl methylphosphonite $CH_3P(OCH_3)_2$ in 10 ml of $CHCl_3$, and, after addition was complete, the mixture was then stirred for 2 hours and, after cooling, worked up. Extraction with 1N $NaHCO_3$ solution, 1N $KHSO_4$ solution and water was carried out, and the organic phase was dried with magnesium sulfate and concentrated in vacuo. The crude product provided, after flash chromatography ($SiO_2$ 70–200 μm+10% $H_2O$; first toluene-+ethyl acetate 20+1, then 1+1 for elution), the title compound in 83% yield.

The compounds I listed in Table 1 were obtained analogously from the starting substances II listed in Table 2 under the reaction conditions listed in Table 3.

NMR - data on the penem I according to the invention

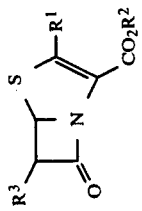

| Example | R¹ | R² | R³ | $^1$H-NMR (CDCl$_3$) : δ (ppm) |
|---|---|---|---|---|
| 1 | 4-CONH₂-C₆H₄-O- | PNB | —CH(OTBDMS)CH₃ | 8.17, 7.55(4H, AA'BB', J=8.7Hz, aromat. H of PNB); 7.83, 7.21(4H AA'BB', J=8.8 aromat. H of benzamide); 5.65(1H, d, J=1.4, H-5); 5.38, 5.21(2H, AB, J=13.8, Benzyl-H); 4.41–4.42(1H, m, —CH(OTBDMS)—); 3.76(1H, dd J=1.4, 4.8, H-6); 1.25(3H, d, J=6.2, CH₃—); 0.82(9H, s. tert.-Butyl-H); 0.09, 0.05(6H, 2×s, Si(CH₃)₂). |
| 2 | 4-CONH₂-C₆H₄-O- | —CH₂CH=CH₂ | " | 7.83, 7.21(4H, AA'BB', J=8.8, aromat. H of benzamide); 5.78–5.94(1H, m, —CH=); 5.62(1H, d, J=1.4, H-5); 5.40–5.17(2H, m, =CH₂); 4.66(2H, m, CO₂—CH₂); 4.25(1H, m, —CH(OTBDMS)—); 3.71(1H, dd J=1.4, 4.8, H-6); 1.25(3H, d, J=6.2, CH₃—); 0.88(9H, s, tert.-Butyl-H); 0.09, 0.05(6H, 2×s, Si(CH₃)₂). |
| 3 | 4-CONH₂-C₆H₄-O- | —CH₂CH₂SiMe₃ | " | 7.82, 7.20(4H, AA'BB', J=8.8, aromat. H of benzamide); 5.61(1H, d, J=1.4, H-5); 4.20–4.30(3H, m, —CH(OTBDMS)— and CO₂CH₂); 3.72(1H, dd J=1.4, 4.8, H-6); 1.25(3H, d, J=6.2, CH₃—); 0.96(2H, m, CH₂Si); 0.87(9H, s, tert.-Butyl-H); 0.1–0.01(total 15H, 3×s, Si(CH₃)₃). |
| 4 | OCH₃ | —CH₂CH=CH₂ | —CH(OTBDMS)CH₃ | 5.85–6.02(1H, m, —CH=); 5.55(1H, d, J=1.4, H-5); 5.43–5.17(total 2H, m, =CH₂); 4.65(2H, m, CO₂—CH₂); 4.25(1H, m, —CH(OTBDMS)—); 4.00(3H, s, OCH₃); 3.65(1H, dd, J=1.4, 4.8, H-6); 1.25(3H, d, J=6.2, CH₃—); 0.90(9H, s, tert.-Butyl-H); 0.10(6H, 2×s, Si(CH₃)₂). |
| 5 | OCH₃ | —PNB | " | 8.20, 7.60(4H, AA'BB, J=8.7Hz, aromat. H of PNB); 5.61(1H, d, J=1.4, H-5); 5.39 and 5.19(2H, ABq, 14Hz, Benzyl-H); 4.25(1H, m, —CH(OTBDMS)—); 4.04(3H, s, OCH₃); 3.71(1H, dd, J=1.4, 4.8, H-6); 1.27(3H, d, J=6.2, CH₃—); 0.82(9H, s, tert.-Butyl-H); 0.09, 0.05(6H, 2×s, Si(CH₃)₂). |

-continued
NMR - data on the penem I according to the invention

| Example | R¹ | R² | R³ | ¹H-NMR (CDCl₃) : δ (ppm) |
|---|---|---|---|---|
| 6 | OCH₃ | —CH₂CH₂SiMe₃ | " | 5.52(1H, d, J=1.4, H-5); 4.25(total 3H, m, —CH(OTBDMS)—, CH₂—OCO); 4.00(3H, s, OCH₃), 3.65(1H, dd J=1.4, 4.8, H-6); 1.25(3H, d, J=6.2, CH₃—); 1.05(2H, m, CH₂Si); 0.90(9H, s, tert.-Butyl-H); 0.5-0.1(15H, 3×s, Si(CH₃)₃). |
| 7 | 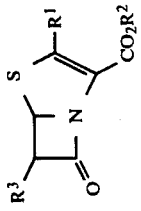 | —PNB | " | 8.29, 7.59(4H, AA'BB', J=8.7Hz, aromat. H of PNB); 5.55(1H, d, J=1.4, H-5); 5.39 and 5.19(2H, ABq, 14Hz, Benzyl-H); 4.72(1H, m, 1'—CH); 4.25(1H, m, —CH(OTBDMS)—); 3.66(1H, dd J=1.4, 4.8, H-6); 2.0-1.5(total 8H, m, Cyclopentyl-CH₂); 1.27(3H, d, J=6.2, CH₃—); 0.82(9H, s, tert.-Butyl-H); 0.08, 0.05(6H, 2×s, Si(CH₃)₂). |
| 8 | 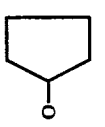 | —PNB | —CH(OTBDMS)CH₃ | 8.19, 7.61(4H, AA'BB', J=8.7Hz, aromat. H of PNB); 5.55(1H, d, J=1.4, H-5); 5.29 and 5.19(2H, ABq, 14Hz, Benzyl-H); 4.21-4.12 (total 3H, m, 1'-CH and —CH(OTBDMS)—); 3.66 (1H, dd, J=1.4, 4.8, H-6); 2.05-1.3(total 10H, m, Cyclohexyl-CH₂); 1.27(3H, d, J=6.2, CH₃—); 0.82(9H, s, tert.-Butyl-H); 0.08, 0.05(6H, 2×s, Si(CH₃)₂). |
| 9 | SCH₃ | —CH₂CH=CH₂ | " | 5.85-6.02(1H, m, —CH=); 5.61(1H, d, J=1.4, H-5); 5.43, 5.37, 5.22, 5.19(total 2H, 4×d, =CH₂); 4.70(2H, m, CO₂—CH₂); 4.22 (1H, m, —CH(OTBDMS)—); 3.68(1H, dd J=1.4, 4.8, H-6); 2.51(3H, s, SCH₃); 1.23(3H, d, J=6.2, CH₃); 0.88(9H, s, tert.-Butyl-H); 0.10(6H, 2×s, Si(CH₃)₂). |
| 10 | SCH₃ | —PNB | " | 8.21, 7.51(4H, AA'BB', J=8.7Hz, aromat. H of PNB); 5.66(1H, d, J=1.4, H-5); 5.41 and 5.21(2H, ABq, 14Hz, Benzyl-H); 4.25(1H, m, —CH(OTBDMS)—); 3.71, 1H, dd j=1.4, 4.8, H-6); 2.52(3H, s, SCH₃); 1.25(3H, d, J=6.2, CH₃—); 0.82(9H, s, tert.-Butyl-H); 0.09, 0.05(6H, 2×s, Si(CH₃)₂). |
| 11 | SCH₃ | —CH₂CH₂SiMe₃ | " | 5.59(1H, d, J=1.4, H-5); 4.0-4.31(zus. 3H, m, —CH(OTBDMS)—, CH₂—OCO); 3.66(1H, dd |

-continued

NMR - data on the penem I according to the invention

| Example | R$^1$ | R$^2$ | R$^3$ | $^1$H-NMR (CDCl$_3$) : δ (ppm) |
|---|---|---|---|---|
| 12 | (tetrahydrofuran-2-yl) | —CH$_2$CH$_2$SiMe$_3$ | —CH(OTBDMS)CH$_3$ | J=1.4, 4.8, H-6); 2.50(3H, s, SCH$_3$); 1.27 (3H, d, J=6.2, CH$_3$—); 1.08(2H, m, CH$_2$Si); 0.89(9H, s, tert.-Butyl-H); 0.01–0.11(15H, 3×s, Si(CH$_3$)$_2$). |
| 13 | (2,5-dihydrofuran-2-yl) | —CH$_2$CH$_2$SiMe$_3$ | —CH(OTBDMS)CH$_3$ | 5.52 and 5.45(total 1H, d, J=1.4, H-5); 5.42–5.35(1H, m, 2'-CH); 4.31–4.15(total 13H, m, —CH(OTBDMS)— and CH$_2$—OCO); 4.03–3.77(2H, m, 5'-CH$_2$); 3.64(1H, m, H-6); 2.51–2.34(1H, m, 3',4'-CH$_2$); 2.05–1.71(3H, m, 3',4'-CH$_2$); 1.25(total 3H, m, CH$_3$—); 1.08(2H, m, CH$_2$Si); 0.87(9H, m, CH$_2$Si and tert.-Butyl-H); 0.09–0.11(15H, m, Si(CH$_3$)$_3$). |
|  |  |  |  | 7.68, 7.52, 6.53(total 3H, 3×m, Furyl-H); 5.56(1H, d, J=1.4, H-5); 4.34–4.21(total 3H, m, —CH(OTBDMS)— and CH$_2$—OCO); 3.69(1H, dd, J=1.4, 4.8, H-6); 1.28(3H, d, J=6.2, CH$_3$—); 1.10(2H, m, CH$_2$Si); 0.91(9H, m, tert.-Butyl-H); 0.01–0.11(15H, 3×s, Si(CH$_3$)$_3$). |
| 14 15 | (phenyl) | —CH$_2$CH$_2$SiMe$_3$ | " | 7.50, 7.39(total 15H, 2×m, Phenyl-H); 5.69 (1H, d, J=1.4, H-5); 4.31(1H, m, —CH(OTBDMS)—); 4.19(2H, m, CH$_2$—OCO); 3.78 (1H, dd, J=1.4, 4.8, H-6); 1.32(3H, d, J=6.2, CH$_3$—); 0.93(total 11H, m, CH$_2$Si and tert.-Butyl-H); 0.01–0.11(15H, 3×s, Si(CH$_3$)$_3$). |
| 16 | (4-CO$_2$CH$_2$CH=CH$_2$-phenyl) | —CH$_2$CH$_2$SiMe$_3$ | —CH(OTBDMS)CH$_3$ | 8.06, 7.53(4H, AA'BB, J=8.8Hz, aromat. H); 6.1–5.94(1H, m, —CH=); 5.71(1H, d, J=1.4, H-5); 5.44–5.20(2H, m, =CH$_2$); 4.84(2H, m, CO$_2$—CH$_2$/Allyl); 4.27(1H, m, —CH(OTBDMS)—); 4.16(2H, m, CO$_2$CH$_2$/TMSE); 3.78(1H, dd, J=1.4, 4.8, H-6); 1.28(3H, d, J=6.2, CH$_3$—); 0.91(9H, s, tert.-Butyl-H); 0.11–0.01(15H, 4×s, Si(CH$_3$)$_2$). |

-continued
NMR - data on the penem 1 according to the invention

[Structure: penem with R³ on β-lactam C, S in ring, R¹ on C=C, CO₂R² group]

| Example | R¹ | R² | R³ | $^1$H-NMR (CDCl₃) : δ (ppm) |
|---|---|---|---|---|
| 17 | cyclobutanone (4-oxocyclobutyl) | —CH₂CH₂SiMe₃ | " | 5.58(d, J=1, 4Hz, H-5); 4.52(m, 1H, Cyclobutyl); 4.25(m, 3H, CO₂CH₂ and C_HCH₃); 3.70(dd, J=5 and 1Hz, H-6); 3.15-3.55(m, 4 Cyclobutyl-H); 1.28(3H, d, J=6Hz, CHC_H₃); 1.08(m, 2H, CH₂Si); 0.88(s, 9H, tert.-Butyl-H); 0.18(s, 6H, Si(CH₃)₂); 0.06(s, 9H, Si(CH₃)₃) |
| 18 | cyclobutanone (4-oxocyclobutyl) | —CH₂CH=CH₂ | " | 5.86-6.03(m, 1=CH); 5.61(d, J=1Hz, H-5); 5.22-5.45(m, 2=CH₂); 4.72(m, 2H, CO₂CH₂); 4.51(m, 1H, Cyclobutyl); 4.25(m, C_HCH₃); 3.72(dd, J=5 and 1Hz, H-6); 3.15-3.55(m, 4-Cyclobutyl-H); 1.28(3H, d, J=6Hz, CHC_H₃); 0.88(s, 9H, tert.-Butyl-H); 0.10(s, 6H, Si(CH₃)₂) |
| 19 | 4,4-dimethoxycyclobutyl | —CH₂CH₂SiMe₃ | " | 5.52(d, J=1Hz, H-5); 4.2-4.32(m, 3H, CO₂CH₂ und C_HCH₃); 4.0-4.14(m, 1H, Cyclobutyl); 3.67(dd, J=5 and 1Hz, H-6); 3.15 and 3.16 (je s, 2×3H, OCH₃); 2.5-2.7(m, 2H, Cyclobutyl); 2.1-2.22(m, 2H, Cyclobutyl), 1.28(3H, d, J=6Hz, CHC_H₃); 1.08(m, 2H, CH₂Si); 0.88(s, 9H, tert.-Butyl-H), 0.10(s, 6H, Si(CH₃)₂); 0.06(s, 9H, Si(CH₃)₃) |

*TBDMS = t-butyldimethylsilyl
Me = Methyl
PNB = para-Nitrobenzyl
TCE = 1,1,2-Trichloroethane
*Compound "14" is prepared from 2 different precursors in Example 14 and 15

TABLE 2

Starting compounds $$\underset{\underset{CO_2R^2}{\overset{O}{\underset{\|}{\overset{\|}{N}}}}}{\overset{R^3}{\underset{O=}{\bigsqcup}}\overset{S-\overset{X}{\underset{\|}{C}}-R^1}{}}$$

| Example | R¹ | R² | R³ | X |
|---|---|---|---|---|
| 1 | —O—C₆H₄—CONH₂ (para) | —PNB | —CH(OTBDMS) | S |
| 2 | —O—C₆H₄—CONH₂ (para) | —CH₂CH=CH₂ | " | S |
| 3 | —O—C₆H₄—CONH₂ (para) | —CH₂CH₂SiMe₃ | " | S |
| 4 | OCH₃ | —CH₂CH=CH₂ | " | S |
| 5 | OCH₃ | —PNB | " | S |
| 6 | OCH₃ | —CH₂CH₂SiMe₃ | " | S |
| 7 | cyclopentyloxy | —PNB | " | S |
| 8 | cyclohexyloxy | —PNB | " | S |
| 9 | SCH₃ | —CH₂CH=CH₂ | " | S |
| 10 | SCH₃ | —PNB | " | S |
| 11 | SCH₃ | —CH₂CH₂SiMe₃ | " | S |
| 12 | 2-tetrahydrofuryl | —CH₂CH₂SiMe₃ | " | O |
| 13 | 2-furyl | —CH₂CH₂SiMe₃ | " | O |
| 14 | phenyl | —CH₂CH₂SiMe₃ | " | O |
| 15 | phenyl | —CH₂CH₂SiMe₃ | " | S |
| 16 | —C₆H₄—CO₂CH₂CH=CH₂ (para) | —CH₂CH₂SiMe₃ | " | O |

TABLE 2-continued

Starting compounds (structure shown)

| Example | R¹ | R² | R³ | X |
|---|---|---|---|---|
| 17 | (cyclobutanone-yl) | —CH$_2$CH$_2$SiMe$_3$ | " | O |
| 18 | (cyclobutanone-yl) | —CH$_2$CH=CH$_2$ | " | O |
| 19 | (cyclobutyl with OCH$_3$, OCH$_3$) | —CH$_2$CH$_2$SiMe$_3$ | " | O |

TABLE 3

Reaction conditions for the cyclization reaction (reaction scheme shown)

| Example | Reagent III | Equivalents of III | Conc. (mmol/l) | Solvent | Temp. (°C.) | Reaction time (h) | Yield % |
|---|---|---|---|---|---|---|---|
| 1 | CH$_3$P(OCH$_3$)$_2$ | 4 | 20 | CHCl$_3$ | 55 | 2 | 83 |
| 2 | " | 3 | 20 | 1.1.2-TCE | 60 | 1 | 57 |
| 3 | " | 4 | 2 | CHCl$_3$ | " | 2 | 62 |
| 4 | CH$_3$P(OC$_2$H$_5$)$_2$ | 4 | 20 | " | " | 0,5 | 38 |
| 5 | " | 4 | 20 | " | " | 0,5 | 55 |
| 6 | " | 4 | 20 | " | " | 0,5 | 48 |
| 7 | " | 4 | 2 | " | " | 2 | 80 |
| 8 | " | 4 | 2 | " | " | 3 | 70 |
| 9 | " | 6 | 20 | " | 55 | 1 | 67 |
| 10 | " | 6 | 20 | " | " | 1 | 61 |
| 11 | " | 6 | 20 | " | " | 1 | 75 |
| 12 | " | 4 | 20 | " | 60 | 3 | 37 |
| 13 | " | 4 | 20 | " | " | 6 | 55 |
| 14 | " | 5 | 20 | " | 55 | 1 | 25 |
| 15 | CH$_3$P(OCH$_3$)$_2$ | 4 | 20 | " | 60 | 0,5 | 20 |
| 16 | CH$_3$P(OC$_2$H$_5$)$_2$ | 4 | 20 | " | " | 1 | 55 |
| 17 | " | 4 | 40 | 1.1.2-TCE | 70 | 2,5 | 72 |
| 18 | " | 4 | 40 | " | " | 2,5 | 58 |
| 19 | " | 4 | 40 | " | " | 2,5 | 42 |

We claim:
1. A process for the preparation of a penem compound I

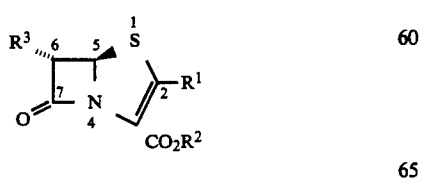

in which
R¹ denotes hydrogen, (C$_1$–C$_4$)-alkyl, (C$_1$–C$_{12}$)-alkoxy, (C$_1$–C$_{12}$)-alkylthio, phenoxy, phenyl (the phenyl rings being unsubstituted or substituted once or twice by carboxyl, (C$_1$–C$_4$)-alkoxycarbonyl, allyloxycarbonyl, aminocarbonyl, (C$_1$–C$_4$)-alkylaminocarbonyl, cyano, F, Cl or Br), (C$_3$–C$_6$)-cycloalkyl, (C$_3$–C$_6$)-cycloalkyloxy, (C$_5$–C$_6$)-oxacycloalkyl (saturated or singly or doubly unsaturated), (C$_3$–C$_6$)-oxocycloalkyl, (C$_3$–C$_6$)-1,1-bis(-C$_1$–C$_3$)-alkyloxy]-cycloalkyl, (C$_3$–C$_6$)-[(C$_1$–C$_3$)-alkylimino]-cycloalkyl, (C$_3$–C$_6$)-[arylimino]cycloalkyl, (C$_3$–C$_6$)-hydroxyiminocycloalkyl, (C$_3$–C$_6$)-(C$_1$–C$_3$-alkyloxyimino)-cycloalkyl, in which the cycloalkyl radical is unsubstituted or substituted once or twice by $C_1$–$C_3$-alkyl, by ($C_1$–$C_3$)-alkoxy, by halogen, or by methylene and is saturated or can contain one or two double bonds, $R^2$ denotes hydrogen or a customary carboxyl protective group which can be eliminated by hydrolysis, photolysis, oxidation, reduction or enzymatically, $R^3$ denotes hydrogen, ($C_1$–$C_4$)-alkyl, ($C_1$–$C_4$)-alkenyl, ($C_1$–$C_4$)-alkoxy, ($C_4$–$C_7$)-cycloalkyl, phenyl, 2-oxo-1,3-dioxolyl, triazolyl, thiazolyl, amino, acylamino or alkoxy, which comprises reacting at between $+10°$ C. and $+70°$ C. a compound of the formula II

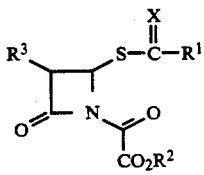

in which

X denotes oxygen or sulfur, and $R^1$, $R^2$ and $R^3$ have the above meaning, with a trivalent organic phosphorus compound of the formula III

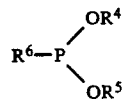

in which $R^6$ denotes ($C_1$–$C_4$)-alkyl, phenyl which can be substituted by ($C_1$–$C_3$)-alkyl or ($C_1$–$C_3$)-alkoxy, and $R^4$ and $R^5$ are identical or different and denote ($C_1$–$C_4$)-alkyl, allyl, benzyl, or phenyl which can be substituted by ($C_1$–$C_3$)-alkyl or ($C_1$–$C_3$)-alkoxy.

2. The process as claimed in claim 1, wherein the reaction of compound II with III is carried out in an organic solvent.

3. The process as claimed in claim 1, wherein $R^1$ denotes hydrogen, ($C_1$–$C_4$)-alkyl, ($C_1$–$C_4$)-alkoxy, ($C_1$–$C_3$)-alkylthio, phenoxy, phenyl (the phenyl nuclei being substituted by ($C_1$–$C_4$)-alkoxycarbonyl, aminocarbonyl or cyano), ($C_5$–$C_6$)-oxacycloalkyl, ($C_4$–$C_6$)-oxocycloalkyl, 3-hydroxyiminocyclobutyl, 3-methoxyiminocyclobutyl, 3,3-dimethoxycyclobutyl, 3-methoxy-2-cyclobuten-1-yl, 2-methoxy-1-cyclobuten-1-yl and 4-methoxy-3-cyclohexen-1-yl $R^3$ denotes 1-hydroxyethyl (in which the OH group is free or protected by trimethylsilyl, diphenyl-tert.-butylsilyl, allyloxycarbonyl, trichloroethoxycarbonyl or 4-nitrobenzyloxycarbonyl), ($C_1$–$C_3$)-alkoxy, ($C_1$–$C_3$)-alkenyl.

* * * * *

UNITED STATES PATENT AND TRADEMARK OFFICE
CERTIFICATE OF CORRECTION

PATENT NO. : 5,198,544
DATED : March 30, 1993
INVENTOR(S) : Karl-Heinz Budt et al.

It is certified that error appears in the above-indentified patent and that said Letters Patent is hereby corrected as shown below:

Column 16, line 63, the portion of the formula reading "$(C_3-C_6)$-1,1-bis(-" should read -- $(C_3-C_6)$-[1,1-bis- --;

line 64, the portion of the formula reading "$C_1-C_3$)-alkyloxy]-cycloalkyl" should read -- $(C_1-C_3)$-alkyloxy]-cycloalkyl --.

Signed and Sealed this

Twelfth Day of April, 1994

BRUCE LEHMAN

Attest:

Attesting Officer

Commissioner of Patents and Trademarks